US009498209B2

(12) United States Patent
Chin

(10) Patent No.: US 9,498,209 B2
(45) Date of Patent: Nov. 22, 2016

(54) ENDOSCOPIC FASCIAL CLOSURE DEVICES AND METHODS FOR USING SAME

(71) Applicant: Pavilion Medical Innovations, LLC, Norwell, MA (US)

(72) Inventor: Albert K. Chin, Palo Alto, CA (US)

(73) Assignee: Pavilion Medical Innovations, LLC, Norwell, MA (US)

( * ) Notice: Subject to any disclaimer, the term of this patent is extended or adjusted under 35 U.S.C. 154(b) by 0 days.

(21) Appl. No.: 14/715,957

(22) Filed: May 19, 2015

(65) Prior Publication Data

US 2015/0245833 A1    Sep. 3, 2015

Related U.S. Application Data

(62) Division of application No. 13/336,837, filed on Dec. 23, 2011, now Pat. No. 9,055,940.

(51) Int. Cl.
| | |
|---|---|
| *A61B 17/04* | (2006.01) |
| *A61B 17/06* | (2006.01) |
| *A61B 17/062* | (2006.01) |
| *A61B 17/34* | (2006.01) |
| *A61B 17/00* | (2006.01) |
| *A61B 17/32* | (2006.01) |

(52) U.S. Cl.
CPC ....... *A61B 17/0485* (2013.01); *A61B 17/0469* (2013.01); *A61B 17/06* (2013.01); *A61B 17/062* (2013.01); *A61B 17/06066* (2013.01); *A61B 17/3474* (2013.01); *A61B 17/0482* (2013.01); *A61B 2017/00535* (2013.01); *A61B 2017/00946* (2013.01); *A61B 2017/0472* (2013.01); *A61B 2017/0474* (2013.01); *A61B 2017/06052* (2013.01); *A61B 2017/320044* (2013.01); *A61B 2090/0811* (2016.02)

(58) Field of Classification Search
CPC   A61B 17/06; A61B 17/062; A61B 17/0485; A61B 17/0482; A61B 2019/4857; A61B 2017/00535; A61B 2017/06052; A61B 17/3474; A61B 2017/00946; A61B 2017/320044
See application file for complete search history.

(56) References Cited

U.S. PATENT DOCUMENTS

| | | |
|---|---|---|
| 5,281,237 A | 1/1994 | Gimpelson |
| 5,387,227 A | 2/1995 | Grice |
| 5,501,691 A | 3/1996 | Goldrath |

(Continued)

OTHER PUBLICATIONS

International Search Report and Written Opinion for PCT/US2011/043102 mailed on Nov. 3, 2011.

(Continued)

*Primary Examiner* — Gregory Anderson
*Assistant Examiner* — Son Dang
(74) *Attorney, Agent, or Firm* — Greenberg Traurig, LLP; Chinh H. Pham; Todd C. Basile

(57) ABSTRACT

A system for closure of a fascial opening is disclosed. The system may include a first capture device for pulling one end of a suture through fascial tissue on one side of a fascial opening, and a second capture device for pulling an opposing end of the suture through the fascial tissue on an opposite side of the fascial opening. A trapping device for locating and engaging the first capture device can be used, prior to the capture device being pulled through the fascial tissue, so that the trapping device can subsequently pull the suture to facilitate closure of the fascial opening. Methods and apparatuses for closure of a fascial opening are also disclosed.

6 Claims, 13 Drawing Sheets

(56) References Cited

U.S. PATENT DOCUMENTS

| | | |
|---|---|---|
| 5,501,692 A | 3/1996 | Riza |
| 5,507,755 A | 4/1996 | Gresl et al. |
| 5,569,269 A | 10/1996 | Hart et al. |
| 6,966,916 B2 | 11/2005 | Kumar |
| 8,066,718 B2 | 11/2011 | Weisel et al. |
| 8,585,714 B2 | 11/2013 | Weisel et al. |
| 8,876,842 B2 | 11/2014 | Marshall et al. |
| 9,055,940 B2 | 6/2015 | Chin |
| 2001/0003158 A1 | 6/2001 | Kensey et al. |
| 2002/0095165 A1 | 7/2002 | Chan |
| 2003/0176874 A1 | 9/2003 | Sauer |
| 2004/0225317 A1 | 11/2004 | Rehnke |
| 2005/0043746 A1 | 2/2005 | Pollak et al. |
| 2006/0069398 A1 | 3/2006 | Suzuki et al. |
| 2007/0179509 A1 | 8/2007 | Nagata et al. |
| 2007/0293876 A1 | 12/2007 | Abe et al. |
| 2008/0243148 A1 | 10/2008 | Mikkaichi et al. |
| 2008/0255591 A1 | 10/2008 | Harada et al. |
| 2009/0216251 A1 | 8/2009 | Levine et al. |
| 2009/0228041 A1 | 9/2009 | Domingo |
| 2009/0234461 A1 | 9/2009 | Rehnke |
| 2009/0259232 A1 | 10/2009 | Shiono et al. |
| 2010/0222876 A1 | 9/2010 | Hyde |
| 2011/0245850 A1 | 10/2011 | Van Der Burg et al. |

OTHER PUBLICATIONS

International Search Report and Written Opinion for PCT/US2012/067564 mailed on Apr. 12, 2013.

ENDOSCOPIC FASCIAL CLOSURE DEVICES AND METHODS FOR USING SAME

RELATED US APPLICATION(S)

The present application is a divisional application of U.S. patent application Ser. No. 13/336,837, filed Dec. 23, 2011, which is incorporated herein by reference in its entirety.

TECHNICAL FIELD

This invention relates generally to surgical closure devices and, more particularly, to closure devices for repairing a hernia and/or fascial opening.

BACKGROUND

A hernia often occurs in a muscle wall of an individual where the muscles have weakened, or where a previous surgical incision was made. Weakened abdominal muscles can result in a ventral hernia, which may produce a bulge or a tear forming in the surrounding tissue. The inner lining of the abdomen, the intestine, or other tissue can then push through the weakened area of the abdominal wall to form a hernia sack or bulge. Where a surgical incision was previously made in the abdomen, portions of the abdominal wall that have been sutured together can separate or tear between sutures over time. This also can result in the inner lining of the abdomen or other tissue pushing through the tear of the abdominal wall to form a bulge or hernia sack.

In large ventral hernias, the defect in the fascial tissue can be about 10 cm wide or greater. The defect may also lie under substantial layers of tissue. Of these layers, the skin is the outermost layer. Beneath the skin is subcutaneous fat, which may be about 5-10 cm or greater. An external fascial layer and a layer of rectus muscle lie beneath the fat, followed by the internal fascia, which is the layer to be closed. In large ventral hernia repair, it may be desirable for the suture to pass through three layers of the abdominal wall—the anterior rectus sheath, the rectus muscle, and the posterior rectus sheath—in order to incorporate all three layers of the abdominal wall into the suture closure.

Tens of thousands of ventral hernia repairs are performed in the United States each year. The conventional surgical repair procedure, or "open" method, requires that a large incision be made in the abdomen of the patient exposing the area of the hernia. The area of the hernia can be reinforced by a surgical mesh and/or closed by sutures. Since a large incision is usually made in the abdomen, the open method of repair can result in increased post-operative pain, an extended hospital stay, a restrictive diet, and an increased risk of surgical complications or infection.

To alleviate some of these issues, laparoscopic procedures have also been developed for repairing ventral hernias. These minimally invasive procedures repair the hernia opening in the abdominal wall using small incisions in the abdomen. Laparoscopes and surgical mesh are typically used in these procedures. In particular, a mesh may be inserted through a trocar and positioned at the surgical site in the abdomen to reinforce the abdominal wall in the area of the hernia. The laparoscopic method of repair can result in decreased post-operative pain and a shorter hospital stay. However, the laparoscopic procedure can also produce some adverse affects. For example, the positioning of the surgical mesh in the abdomen can result in the mesh irritating the intestines or other abdominal contents. In addition, the surgical mesh can move in the abdomen from its original position, exposing the hernia site and creating the potential for the development of another ventral hernia.

Methods of closing the hernia using a suture, however, typically are not performed in laparoscopic ventral hernia repair for a variety of reasons. In particular, laparoscopic suturing may be difficult to perform since manipulation of the needle takes place in a confined space, typically under the skin, where the angle of tissue access for suture placement is often determined by trocar port site selection. Additionally, since fascial openings may be large, it may be difficult or impossible to thread a suture through opposing sides of the fascia using a needle and/or traditional laparoscopic equipment when working via laparoscopic incisions or needle punctures. Furthermore, substantial tension is required to bring the edges of the fascia together in large ventral hernias. It may also be difficult or impossible to apply a large amount of tension to suture and tie knots in the suture using traditional laparoscopic instrumentation.

In some laparoscopic hernia repair, a surgeon can use a technique where a suture passer is inserted through a midline incision in order to grasp suture ends at the edge of the fascial opening, and pull them out through the midline incision for subsequent tying. However, if the hernia is large or the patient is obese, using a suture passer in this way may be difficult or impossible because the edges of the fascial opening may be relatively distant from the midline and/or the suture may have to pass through multiple layers of tissue for closure. Since suture passers are typically rigid, the angle at which the suture passer is inserted in order to reach from the midline to the edge of the opening in a large hernia may be severe, making it difficult or substantially impossible to grasp the suture end and subsequently draw it out of the midline incision. It may be desirable, instead, for a device that can grasp the suture to be inserted at an angle substantially perpendicular to the skin.

Another technique for repairing a ventral hernia using a suture is known as the Components Separation ("CS") Method. The CS method attempts to reduce hernia recurrence by reducing tension caused by sewing the defect closed. Using this method, a surgeon typically creates a large, open incision in the abdomen, then bluntly dissects the external and internal oblique muscles from the overlying skin, the underlying posterior rectus sheath, and from each other. The surgeon can then shift the layers of tissue so the fascial opening is moved toward the abdominal midline. Shifting the defect prior to sewing the defect closed can reduce tension on the defect and any suture used to close the defect.

Accordingly, it would be desirable to have an effective fascial closure system that can deliver sutures to the site of a fascial opening through laparoscopic incisions or punctures in order to close the opening, while minimizing or reducing the likelihood of tearing.

SUMMARY OF THE INVENTION

A system for closure of a fascial opening is disclosed. The system may include a first capture device for pulling one end of a suture through fascial tissue on one side of a fascial opening, and a second capture device for pulling an opposing end of the suture through the fascial tissue on an opposite side of the fascial opening. A trapping device for locating and engaging the first capture device can be provided, prior to the capture device being pulled through the fascial tissue, so that the trapping device can subsequently pull the suture through the trapping device to facilitate closure of the fascial opening. Methods and apparatuses for closure of a fascial opening are also disclosed.

In an embodiment, the capture devices may include a grasping mechanism at their distal ends, so that they can grasp, retain, and pull the suture. The grasping mechanism may be a hook, loop, or other device that can grasp and/or hold the suture.

The first and second capture devices, in an embodiment, may be needles or trocars that can be directly inserted through the skin and/or fascial tissue.

The trapping device, on the other hand, may have its distal end shaped for dissecting tissue so that the trapping device can tunnel through intervening tissue as it is advanced to the site of delivery. In some instances, the distal end may be sharpened, beveled, tapered, or blunt to facilitate sharp and/or blunt dissection.

The trapping device can also include an opening that the first or second capture device can enter so that the first or second capture device can subsequently thread the suture through the opening. A trap may be provided that allows the first or second capture device to enter the opening, and minimizes the occurrence of the first or second capture device exiting the opening, so that the trapping device can retain the first or second capture device within the opening. The trap can be a clasp, a slot, or any other device for trapping a capture device within the opening.

The system may further include a knot pusher for pushing a knot tied in the suture toward the site of the fascial opening.

In an embodiment, a delivery device for placing the ends of the suture on opposite sides of the fascial opening so they can be captured by the first and/or second capture devices, can be provided. The delivery device may include an extension for presenting the ends of the suture for capture at the site of the fascial opening. The delivery device can also include a fastener that holds the ends of the suture during advancement of the delivery device, and positions the ends of the suture at the site of delivery for capture.

In another embodiment, a method for closure of a fascial opening includes positioning one end of a suture on one side of a fascial opening, and an opposing end of a suture on an opposing side of the fascial opening. The end of the suture can be accessed, through the fascial tissue, with a device for grasping the suture and pulling the end of the suture through the distal portion of a trapping mechanism. The trapping mechanism may be retracted, so as to pull the one end of the suture across the fascial opening and towards the opposing end of the suture for subsequent closure of the fascial opening.

Accessing the suture may include grasping the one end of the suture with a grasping mechanism that extends from a distal end of the capture device, and can retract into the device so as to hold the suture securely.

In an embodiment, a trapping mechanism can be used to subcutaneously locate the device for grasping. The suture may then be threaded through an opening in the trapping mechanism, and subsequently the trapping mechanism can subsequently pull the end of the suture across the fascial opening. A portion of the suture can be drawn through a second incision and outside of the body so that the ends can be subsequently tied in a knot in order to hold the fascial opening in a closed position. The knot can be pushed, with a knot pushing device, toward the fascial opening in order to impart tension on the suture at the site of the fascial opening.

In some embodiments, the opposing end of the suture can also be engaged by a second device for grasping the suture.

The method can also include, prior to the step of positioning, laparoscopically separating layers of tissue from each other to allow shifting of the fascial opening toward an abdominal midline, so as to reduce tension once the opening is closed.

In another embodiment, trapping apparatus includes an elongated body for placement adjacent to a fascial opening, and for locating and engaging a device used in connection with closure of a fascial opening. The apparatus can include gap in a distal portion of the body sufficiently sized for encircling the device and for snaring a suture from the device.

A trapping mechanism may be designed to secure the suture within the gap for subsequent puling of the suture across the fascial opening to close the opening. In some embodiments, the trapping mechanism can be a spring loaded strip that becomes deflected by the surgical device to allow the surgical device to enter the hole. The strip may be biased in a closed position to prevent surgical device from exiting the hole. The trapping mechanism may also be provided with a tunneling mechanism for dissecting tissue as the trapping mechanism is advanced under the skin.

In another embodiment, a suture delivery apparatus includes a hollow body for accommodating a suture therewithin. An extension may protrude from the body for presenting the ends of the suture for capture. A fastener may be provided for holding the ends against the extension while the apparatus is advanced to the site of a fascial opening, and for allowing, once the ends are captured, the suture to be delivered from within the body to the site.

The band can be situated about the distal portion of the body. In some embodiments, the band may be placed through a groove at the distal end of the body to prevent movement of the band during delivery. The band can also be elastic so as to hold the ends of the suture against the body by pressing the ends against the body.

In some embodiments, the suture delivery apparatus can also include a valve that can be opened or closed in order to control a gas insufflation at a surgical site.

DESCRIPTION OF SPECIFIC EMBODIMENTS

Figure 1:
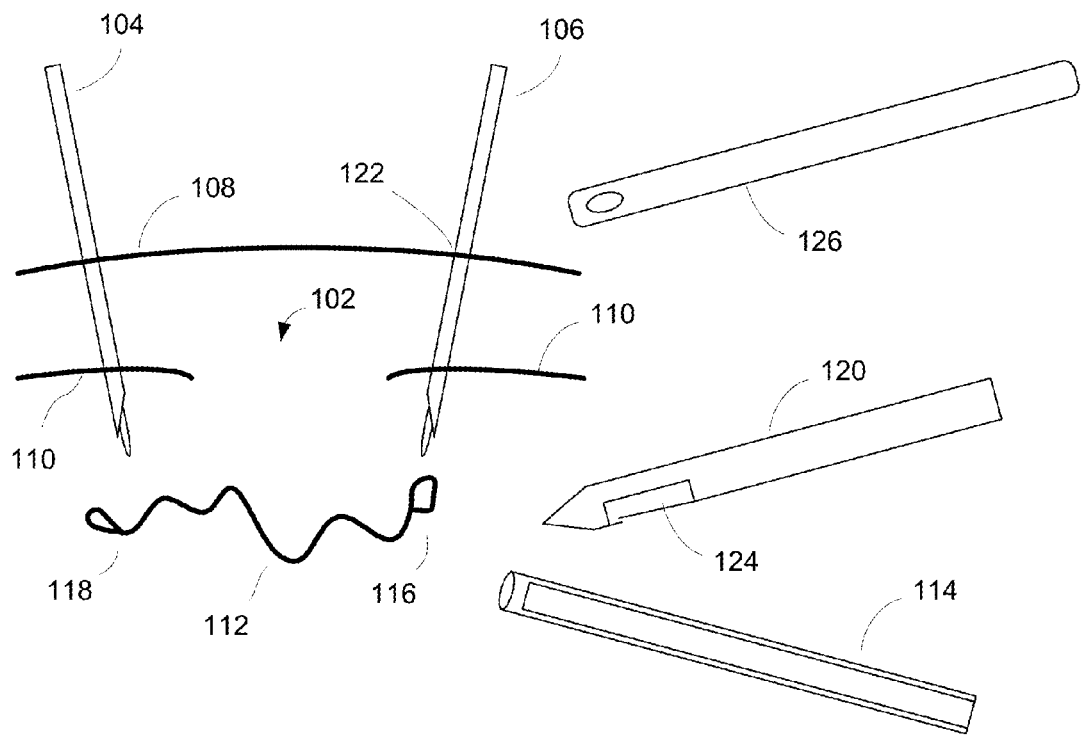
FIG. 1 depicts a system for closing a fascial opening.

In accordance with one embodiment of the present invention, systems and methods are provided for closure of a fascial opening. FIG. 1 shows an example of such a system 100, which may be used to deliver sutures to the site of a fascial opening 102 (e.g. a hernia or other opening), for the purpose of closing the fascial opening 102. System 100 may be designed to deliver the sutures and to subsequently close the opening by manipulating the sutures through minimally invasive or laparoscopic surgery, for example through small incisions or punctures in the skin. As shown in FIG. 1, in order to close the fascial opening, a system 100 may include various devices including, but not limited to: suture capture devices 104 and 106, delivery device 114, trapping device 120, and knot pusher 126. These devices, and their operation, will be discussed below in greater detail.

Although described as systems and methods for closing a fascial opening, one skilled in the art will recognize that the system and methods may be used for any procedure requiring closure of an opening. It should be appreciated that the devices of the present invention can be adapted for use to close other openings in the body. For example, the endoscopic fascial closure system of the present invention may also find use in other types of hernias, or in other types of openings in tissue or organs. Additionally, the systems and methods described need not be limited to laparoscopic or minimally invasive surgery; they can be used during laparotomy or other large incision surgeries.

Closure System

As shown in FIGS. 2A-2F, system 100 may include a delivery device 114 for delivering suture 112 to the site of fascial opening. Delivery device 114 may be configured to deliver each end of suture 112 to an opposite side of the fascial opening 102. For instance, delivery mechanism 114 may deliver the first end of suture 112 (e.g. end 118) to a first side of fascial opening 102, and an opposite end of suture 112 (e.g. end 116) to an opposite side of fascial opening 102. The order of delivery may also be reversed or altered as desired.

Delivery device 114 may include a hollow body 202 for accommodating suture 112. In some embodiments, body 202 may be a rigid tube that can be inserted under the skin of a patient in order to direct suture 112 to the site of fascial opening 102. Body 202 may protect suture 112 from entanglement as it is advanced to the site of delivery. To that end, body 202 may be made from graphite, plastic, metal, or any material that can provide sufficient rigidity to direct suture 112 to fascial opening 102. Body 202 can also be made from a flexible material, or made of a shape memory material, if desired, so that it can be bent or shaped during delivery, so long as it can be advanced to the site of delivery and minimize or prevent entanglement of suture 112. Additionally, body 202 can have any diameter sufficiently large to accommodate suture 112 therewithin, and sufficiently small to be inserted into the body through a laparoscopic incision, or through a trocar port, trocar, needle, or other device that can provide a pathway through the skin. Since body 202 in intended to be inserted under the skin, body 202 may be made from a biocompatible material suitable for surgical operations.

In an embodiment, delivery device 114 may include an extension 204 from body 202 that can present the ends of suture 112 to the site of fascial opening for delivery. The extension 204 can be fixed or movable with respect to body 202 so as to allow a user of delivery device 114 to maneuver the ends 116 and 118 of suture 112 to facilitate delivery.

Figure 2A:
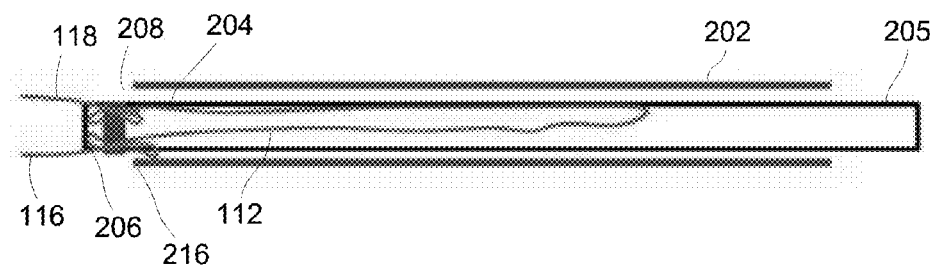
FIGS. 2A-2F illustrate various views of embodiments of a delivery device for delivering a suture to the site of a fascial opening.

In some embodiments, as shown in FIG. 2A, the extension 204 may be provided by a rod 205, or coupled to a distal end of rod 205, so that the extension 204 can slide and/or rotate relative to body 202. In such a design, rod 205 can slide along the length of body 202 so that its distal end 206 can extend from exit end 208 of body 202. As rod 205 extends from body 202, it may facilitate delivery of suture 112 by presenting the ends 116 and 118 of suture 112 to the site of delivery. Rod 205 can also rotate with respect to a longitudinal axis of body 202 in order to maneuver ends 114 and 116. Such rotation and extension can allow the ends of suture 112, which may be fastened to the distal end of rod 205, to be advantageously placed for delivery at the site of fascial opening 102.

Figure 2B:
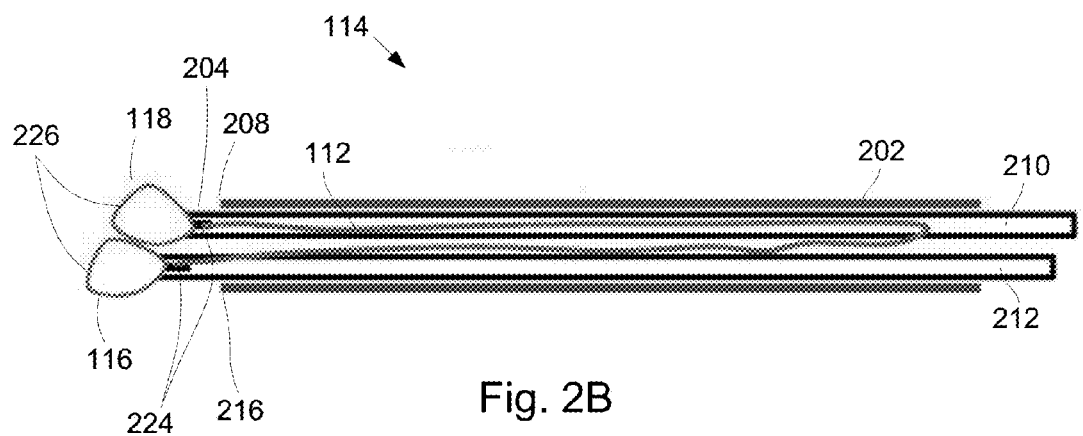

In other embodiments, as shown in FIG. 2B, the extension 204 may be provided by multiple rods 210 and 212. In such a configuration, each end of suture 112 may be fastened to a distal end of one of the rods 210 and 212 so that the ends 116 and 118 of suture 112 can be individually extended from body 202 and maneuvered for placement at the site of fascial opening 102. Each rod 210 and 212 may slide along the length of body 202 and/or rotate with respect to a longitudinal axis of body 202, so that the ends 116 and 118 can be advantageously placed for delivery.

Figures 2C, 4G:
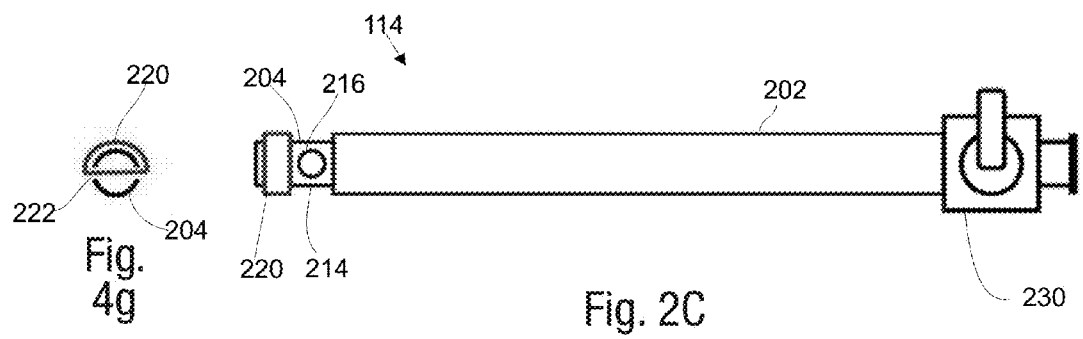

FIG. 2C shows another embodiment of a delivery device 114, where, as shown, the extension 204 may be a fixed, distal section 214 of body 202 that can present suture 112 to the site of delivery. In such embodiments, the section 214 may be coupled to, attached to, or part of body 202 so that, as body 202 is maneuvered and rotated, section 214 is also maneuvered and rotated, and thus can position suture 112 at the site of fascial opening 102 for delivery. Although section 214 is shown with a diameter that is smaller than that of body 202, section 214 can have any diameter or geometric shape that allows delivery device 114 to be advanced under the skin to a site of delivery.

Figure 2D:
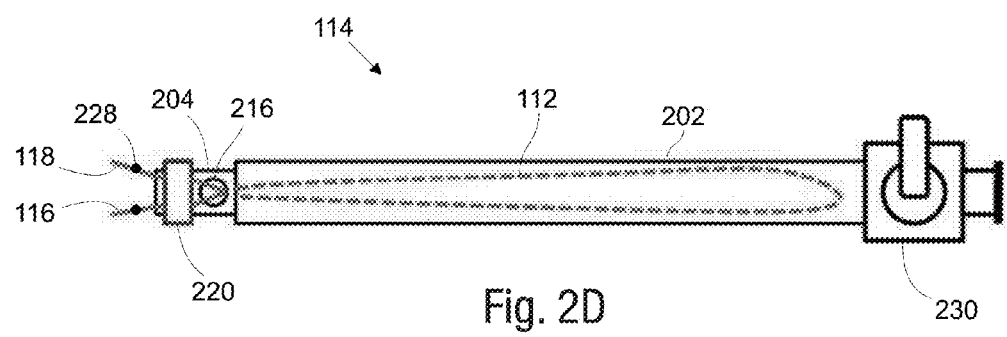
Figure 2E:
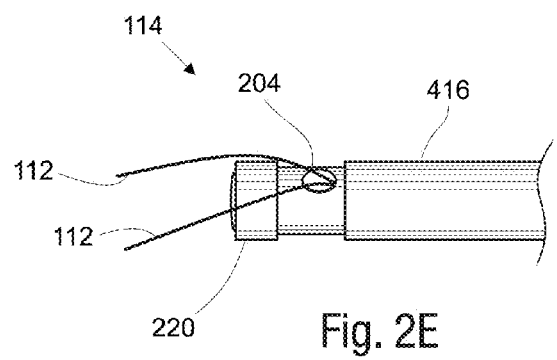
Figure 2F:
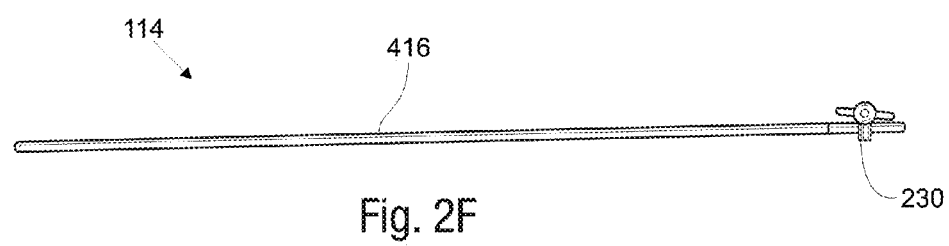

Looking now at FIGS. 2A-2D, since suture 112 can be accommodated within body 202, delivery device 114 may, in an embodiment, include an opening 216 so that suture 112 can be removed from within body 202 during delivery. In some designs, opening 216 can be an opening in exit end 208 of delivery device 114, as shown in FIGS. 2A-2B. In other designs, opening 216 can be an opening in extension 204, as shown in FIGS. 2C-2D. In such a design, the axis of opening 216 can be substantially transverse to body 202, or at any other angle to allow delivery of suture 112 from within body 202. Of course, opening 216 can be situated in any other location that allows delivery of suture 112 from within body 202 to the site of fascial opening 102.

In any of the embodiments shown in FIGS. 2A-2F, a fastener may be used to secure the ends 116 and 118 of suture 112 to the extension 204 so that the ends 116 and 118 can be held securely against the extension as delivery device 114 is advanced under the skin to the site of delivery. The fastener, in an embodiment, can be a groove, a slot, an adhesive, or any other mechanism for securely fastening ends 116 and 118 to extension 204.

In some embodiments, the fastener can be a band 220 situated about extension 204, as shown in FIGS. 2A and 2C-2E. The end of suture 112 may be placed between band 220 and extension 204 so that as delivery device 114 is advanced under the skin, the ends do not become loose, and so once suture 112 is positioned for delivery, suture 112 can be pulled out from between band 220 and extension 204.

The band 220, in an embodiment, may be elastic in nature so that it can hold suture 112 against extension 204. Accordingly, the band may be made of silicon, rubber, or any other elastic material. The band 220 may also be made from a biocompatible material since it may be inserted into a patient's body. In some cases, the band 220 may fit into grooves 222 in the distal end of extension 204, as shown in FIG. 2G. This may minimize movement of band 220 as delivery device 114 is advanced to the site of fascial opening 102.

In another embodiment, the fastener may include one or more grooves 224 (FIG. 2B), within which the ends 116 and 118 can be placed. In such an embodiment, placing the ends of suture 112 in the grooves can allow suture 112 to be pulled from the grooves 224 and remain at the site of fascial opening 102 during delivery.

To facilitate delivery, the ends of suture 116 can include loops 226 (as shown in FIG. 2B) or knots 228 (as shown in FIG. 2D). Loops 226 and knots 228 may allow suture 112 to be more easily snared or grasped by a capture device during delivery, as will be discussed below. The loops 226 and knots 228 can also act to prevent the ends of suture 112 from slipping underneath band 220, or otherwise becoming unfastened, from extension 204. Of course, suture 112 can include other mechanisms, such as bends or hooks, to facilitate delivery.

Delivery device 114 can also include a mechanism 230 to provide fluid insufflation to the surgical site. As shown in FIGS. 2C and 2D, mechanism 230 can be a valve, stopcock, petcock, or other device that can control fluid flow and pressure.

Figure 3A:
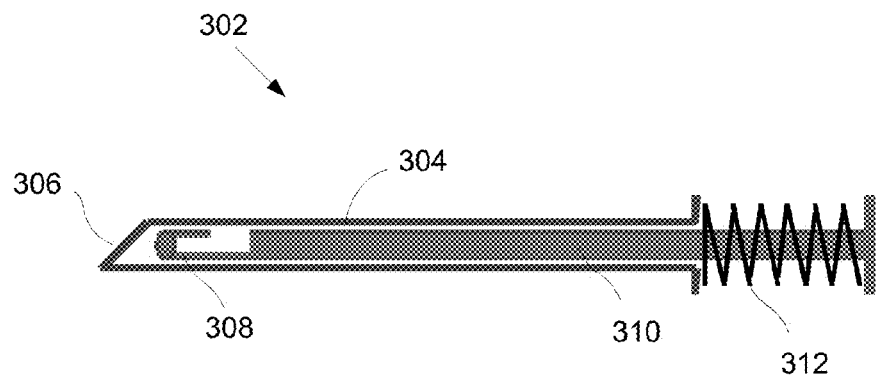
FIGS. 3A-3D show various embodiments of capture devices for capturing a suture at the site of a fascial opening.
Figure 3B:
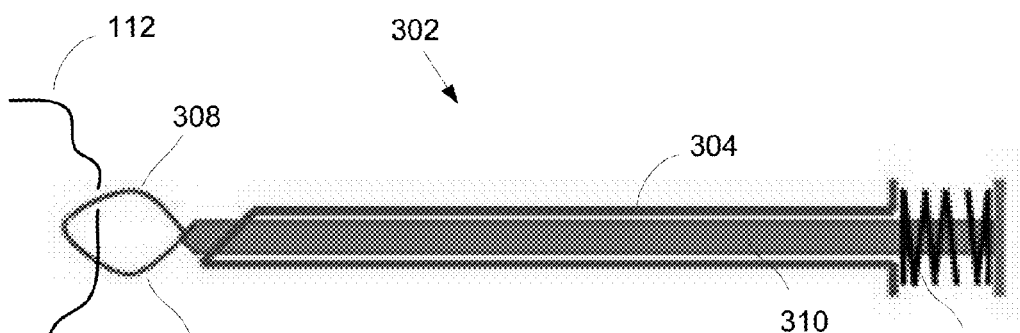
Figure 3C:
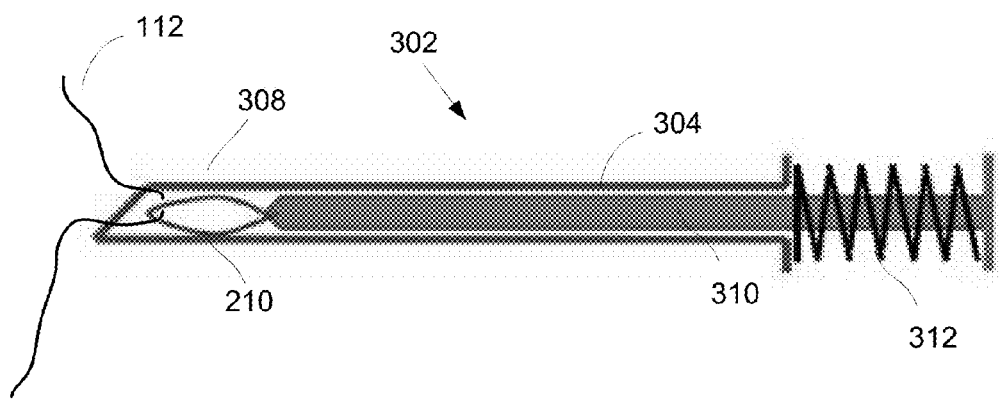

As suture 112 is delivered to the site of fascial opening 102, it may be advantageous to grasp and hold suture 112 so that it can remain at the site of fascial opening 102 while delivery device 114 is removed. Accordingly, system 100 may include capture devices 104 and 106 that can grasp the ends of suture 112 once they are placed at the site of fascial opening 102. FIGS. 3A-3C show examples of a capture device 302 for such grasping and holding of suture 112.

Referring now to FIGS. 3A-3C, capture device 302 may include a body 304 that can be inserted through the skin to the site of fascial opening 102. In an embodiment, body 304 may be tubular so that it can puncture the skin or be inserted through a laparoscopic incision. Of course, body 304 may have any other shape as well that allows capture device 302 to be inserted through the skin in order to capture suture 112.

In an embodiment, capture device 302 can be used as a needle or trocar so that it can directly pierce the skin and/or fascial tissue without the need for an external trocar. Accordingly, body 304 may have a beveled or tapered distal end 306 that be inserted through a laparoscopic opening, or can penetrate through skin 108 and/or fascial tissue 110. In particular, distal end 306 can be sufficiently sharp so that it can pierce the tissue. In certain instances, the inner edge of distal end 306 can be rounded to minimize damage to suture 112 when capture device 302 and suture 112 come in contact with each other.

In an embodiment, capture device 302 can accommodate a grasping mechanism 308 within body 304. Grasping mechanism 308 may be used to grasp and retain suture 112 as suture 112 is delivered to the site of fascial opening 102. Once suture 112 is captured by grasping mechanism 308, suture 112 can be pulled from delivery device 114 and remain at the site of delivery. In some embodiments, grasping mechanism 308 may be a hook (as shown in FIG. 2A) or loop (as shown in FIGS. 2B and 2C) to facilitate capturing suture 112. Grasping mechanism 308 can be constructed from wire, metal, plastic, rubber, or other material suitable for surgery. Of course, grasping mechanism 308 may also include other mechanisms for grasping suture 112, including, but not limited to, a fork, one or more fingers, a clamp, etc.

Grasping mechanism 308 may also be designed to extend from and retract into body 304 to facilitate insertion of grasping mechanism 308 into the body, and to facilitate capture of suture 112. When grasping mechanism 308 is retracted, distal end of body 304 can be inserted through the skin 108 and fascial tissue 110 without interference from grasping mechanism 308, as shown in FIG. 3A. Grasping mechanism 308 can then extend from the distal end 306 of body 302 so that it can capture suture 112, as shown in FIG. 3B. Once captured, grasping mechanism 308 may be designed to retract back into body 304 so that it can draw suture 112 into body 202 in order to hold and retain suture 112, as shown in FIG. 3C.

In an embodiment, grasping mechanism 308 can expand when extended from body 304, and contract when retracted into body 304, in order to facilitate capture of suture 112. For example, FIG. 3B shows grasping mechanism 308 in an expanded state and having a relatively large diameter. Once retracted into body 304, as shown in FIG. 3C, grasping mechanism 308 may be compressed. In the compressed state, grasping mechanism may be able to pinch, press, and/or bend suture 112 so that suture 112 is held fast.

As discussed above, suture 112 may have a loop at its ends to facilitate capture by grasping mechanism 308. For example, grasping mechanism 308 may hook the loop in order to capture suture 112. Of course, the loop need not be at the end of suture 112—it may be situated anywhere along suture 112 to facilitate capture.

Capture device 302 may also include an activation mechanism 310, for extending grasping mechanism 308 from the distal end 306 of capture device 302. In an embodiment, the activation mechanism 310 may be biased so that grasping mechanism is normally retracted within body 304. As shown in FIGS. 3A-3C, activation mechanism may be a rod that can extend grasping mechanism 308 from distal end 306 of capture device 302. In some embodiments, a spring 312 that can be coupled to the rod, as shown, so that grasping mechanism 308 can be biased to a withdrawn position. Once a force is applied to the rod, in opposition to the force applied by spring 312, the rod and grasping mechanism 308 can move along the length of capture device 302 so that grasping mechanism can extend from distal end 306. Of course, other designs that can extend grasping mechanism 308 are within the scope of the invention, including, but not limited to: pneumatic, hydraulic, electronic, or mechanical mechanisms, or combinations thereof.

Figure 3D:
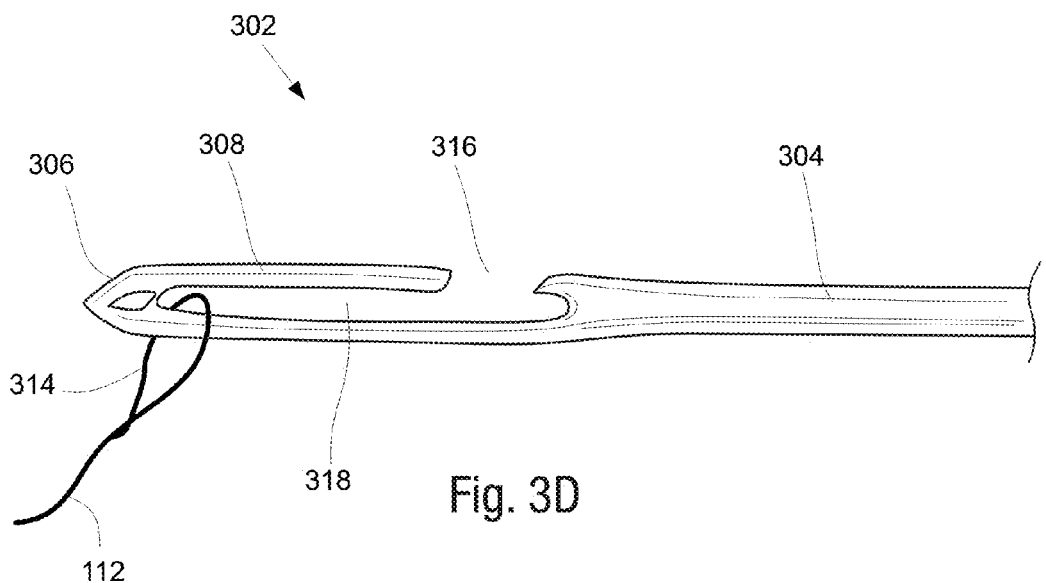

In another embodiment, as shown in FIG. 3D, capture device 302 may include a grasping mechanism 308 that may be integral to or continuous with body 304. Such a design may provide capture device 302 with axial strength and/or rigidity for insertion through tissue. In such an embodiment, grasping mechanism 308 may include a hook or other device that can hook or snag or capture a looped end 314 of suture 112 underneath the skin. The looped end 314 can be formed by tying, molding, heat-pressing, or any other method of forming a loop in suture 112. Once hooked, grasping mechanism 308 can hold, retain, or otherwise manipulate looped end 314 of suture 112 under the skin.

Suture capture device 302, as shown in FIGS. 3A-3D for example, may be sufficiently strong and/or rigid so it can be inserted through multiple layers of tissue. If the fascial opening is large, or the patient obese, it may be desirable to thread suture 112 through at least three layers of tissue in the abdomen—the anterior rectus sheath, the rectus muscle, and the posterior rectus sheath—in order to close the hernia. Accordingly, suture capture device 302 may be sufficiently rigid and/or strong so that it can be inserted, substantially perpendicular to the skin, and pierce through these layers in order to capture suture 112 and subsequently pull suture 112 through the layers.

Figure 4:
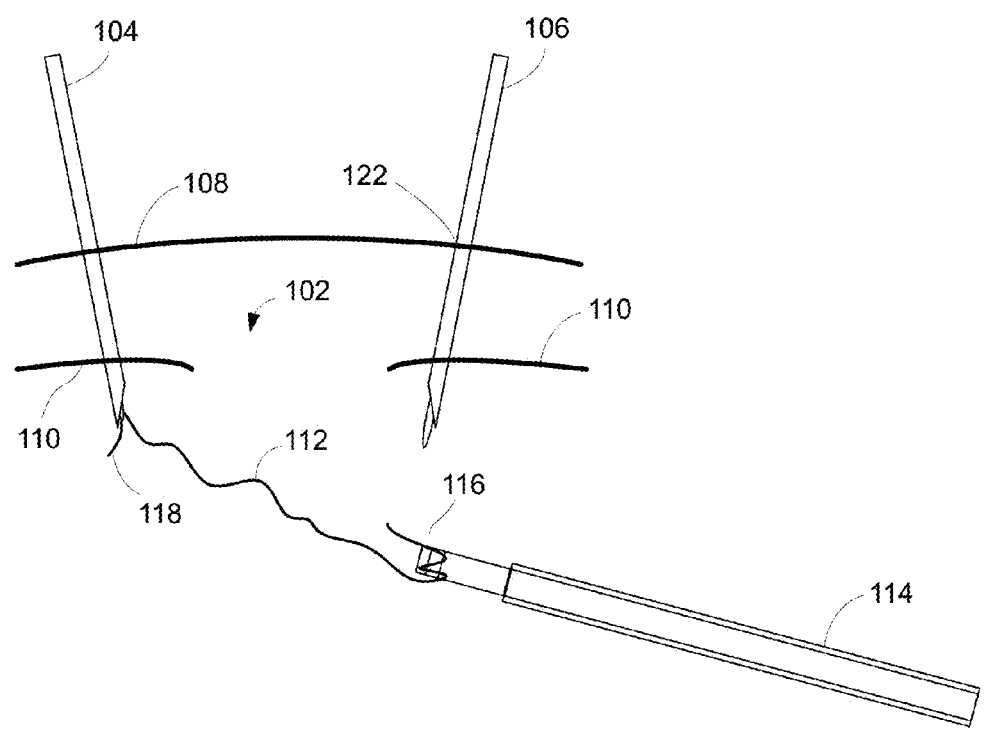
FIG. 4 shows suture capture devices of the system of FIG. 1, positioned at the site of a fascial opening.

FIG. 4 shows an example of suture capture devices placed on opposing sides of fascial opening 102 to capture suture 112. As shown, suture capture device 104 may be inserted through an incision or puncture in skin 108, and may penetrate fascial tissue 110 on one side of fascial opening 102. Similarly, suture capture device 106 may be inserted through a second incision or puncture in skin 108, and may penetrate fascial tissue 110 on an opposing side of fascial opening 102. Delivery device 114 may then be advanced to the site of fascial opening, and may present one end 118 of suture 112 to capture device 104 for capture, then another end 116 of suture 112 to capture device 106 for capture. Since capture devices 104 and 106 have been inserted through fascial tissue 110, they may be withdrawn through fascial tissue 110 in order to thread suture 112 through opposing sides of the fascial opening 102 for subsequent closure of fascial opening 102.

Once suture 112 is delivered to the site of fascial opening 112, a surgeon may wish to manipulate suture 112 so it can be used to close fascial opening 102. However, locating the suture 112 under the skin can be difficult or substantially impossible due to the ductile nature of the suture and the surrounding tissue. It may be easier and more efficient to locate one of the capture devices that has been inserted through fascial tissue 110, because the capture devices can have relatively rigid bodies 304. Accordingly, fascial closure system 100 may include a trapping device 120 that can be inserted under the skin to locate and trap one of the capture devices 104 and/or 106.

As shown in FIGS. 5A-5D, trapping device 120 may include a body 502 that can be directed under the skin to the site of fascial opening 102. Body 502 can be substantially tubular, and can have a relatively small diameter (e.g. 3 mm) so that it can tunnel through and dissect tissue as it is advanced under a patient's skin to the site of fascial opening 102. Body 502 can also have other geometric shapes and other diameters, as long as body 502 can tunnel beneath the skin to locate capture device 104 or 106.

In some embodiments, body 502 can be rigid, or semi-rigid for advancement and dissection of tissue under the skin. To the extent desired, body 502 can also be flexible for purposes of maneuverability, depending upon the application. Accordingly, body 502 may be constructed from metal, plastic, rubber, or any other material that can provide the necessary rigidity and flexibility. Since body 502 may be inserted under the skin, it may also be constructed from a material that is biocompatible.

In some embodiments, body 502 may include a distal end 504 that can tunnel through tissue. The tunneling distal end 504 may dissect tissue such as subcutaneous fat, muscle, etc., as body 502 is advanced under the skin. In an embodiment, to facilitate dissection, distal end 504 may be beveled or tapered. In other configurations, distal end 504 may be sharp to facilitate sharp dissection, or may be relatively blunt to facilitate blunt dissection. In some embodiments, a dissection mechanism, such as a pointed end, a blade, a needle, an apple cutter, a grate, or any other mechanism that can dissect, can be coupled to distal end 504.

Trapping device 120 can be designed to provide tactile feedback to a user, so that the user can use trapping device 120 to locate another device, such as capture device 104, under the skin. When contact is made between trapping device 120 and capture device 104, the user holding trapping device 120 and/or capture device 104 may feel the contact so he or she can subsequently use trapping device 120 to trap capture device 104. In such an embodiment, trapping device 120 and/or capture device 104 can be constructed in such a way, and/or constructed from a material, that allows such tactile feedback to be felt by the user.

Body 502 may also have a mouth or gap 506 near its distal end. The mouth or gap may be sufficiently large so that, once trapping device 120 locates capture device 104 under the skin, capture device 104 can be directed into the gap 506.

Figure 5A:
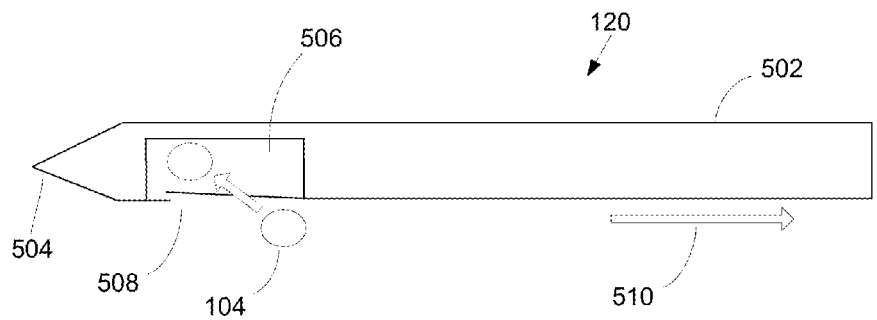
FIGS. 5A-5D depict various embodiments of a trapping device for tunneling through tissue and trapping a suture at the site of the fascial opening.
Figure 5B:
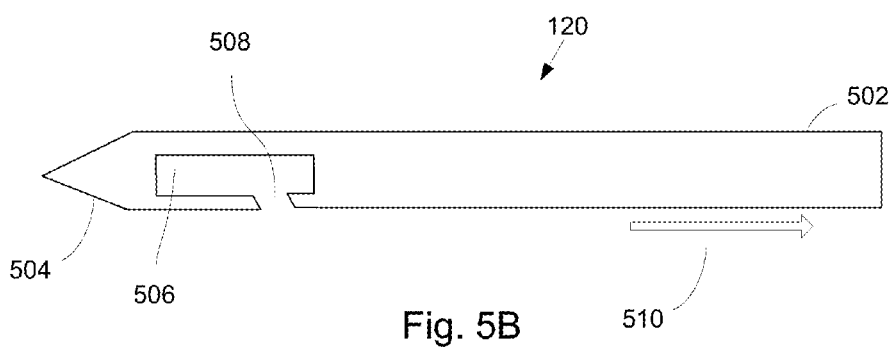

In some instances, once capture device 104 has entered, it may be desirable to prevent capture device 104 from subsequently exiting gap 506 so that capture device 104 can subsequently thread suture 112 through gap 506. Accordingly, trapping device 120 may have a trap 508 that allows capture device 104 to enter gap 506, but prevents or minimizes the chance that capture device 104 can exit. In some embodiments, trap 508 may be a plastic or metal clip, as shown in FIG. 5A. The clip may be biased or spring loaded so that it can be pushed open as capture device 104 enters gap 506, and can subsequently close once capture device 104 has entered gap 506. In other embodiments, trap 508 may be a slot, as shown in FIG. 5B. The slot may have a size sufficiently large to allow capture device 104 to enter gap 506, and sufficiently small to minimize the chance that capture device 104 can exit gap 506. The slot may also be located at a proximal end of gap 506 so that, as trapping device 120 is pulled in the direction of arrow 510, capture device 104 can remain within gap 506.

One skilled in the art will recognize that capture device 302, as shown in FIG. 3D, also includes a slot 316 and gap 318. Therefore, to the extent desired, a capture device 302, such as the capture device 302 as shown in FIG. 3D, can be used to tunnel through tissue and trap suture 112 and/or capture device 104. To the extent desired, slot 316 and gap 318 can be made large enough so that capture device 104 be trapped within gap 318, as described above.

As shown, the clip (FIG. 5A) and slot (FIG. 5B) can be configured to allow capture device 104 to enter gap 506 as trapping device 120 is pulled in the direction shown by arrow 510. For example, the clip (FIG. 5A) may be hinged so that it opens on its distal side, and/or opens inward, as capture device 104 presses against it. This can allow capture device 104 to enter gap 506 as trapping device is pulled alongside capture device 104 in the direction of arrow 510. As another example, the slot (FIG. 5B) can have beveled edges that can direct capture device 104 into gap 510 as trapping device is pulled in the direction of arrow 510.

Figure 5C:
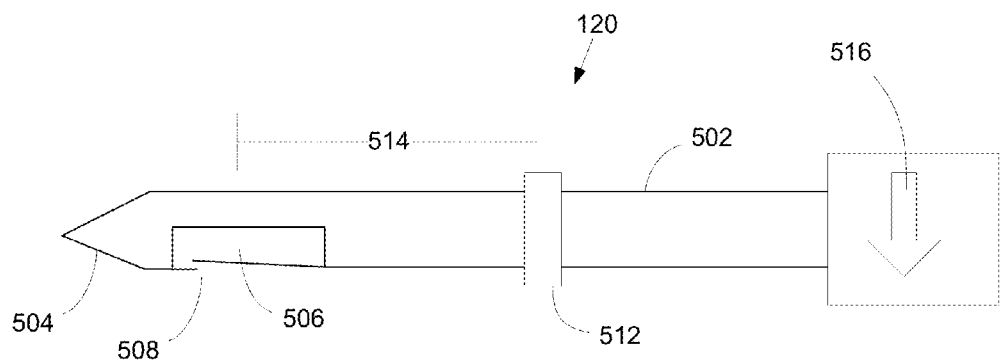

Since trapping device 120 may be used under the skin, trapping device 120 may have features that aid a surgeon in maneuvering trapping device 120 to the site of fascial opening 102 and locating capture device 104. For example, as shown in FIG. 5C, trapping device 120 may have a marker 512, which may be used to gauge a how far trapping device 120 should be inserted in order to trap suture capture device 104. In some embodiments, marker 512 may be able to slide along the length of trapping device 120, allowing a surgeon to set marker 215 at a predetermined depth 514, so that the surgeon knows how far he should insert an incision through which capture device 104 is inserted and an incision through which trapping device 120 is to be inserted, in order to estimate how far trapping device 120 should be advanced under the skin in order to locate and trap capture device 104. Marker 512 may then be adjusted so that, once trapping device 120 is inserted to the depth indicated by marker 512, opening 508 is positioned to trap suture capture device 104 under the skin.

Additionally, marker 512 may act as a stop so that trapping device 120 is not inserted too far into the body. For example, marker 512 may have a diameter slightly larger than trapping device 120, or may otherwise protrude from trapping device 120, so that once trapping device 120 is inserted through a small incision to the depth indicated, marker 512 by press against the surface of the skin and prevent trapping device 120 from advancing further. Although depicted in FIG. 5C as an adjustable ring, marker 512 may be any marker capable of marking distance 514 and/or protruding from trapping device 120.

Trapping device 120 may also include indicator 516, which may identify the direction from which capture device 104 can enter opening 508. The indicator 516 may aid the surgeon in rotate and manipulate trapping device 120 in order to trap capture device 104.

Figure 5D:
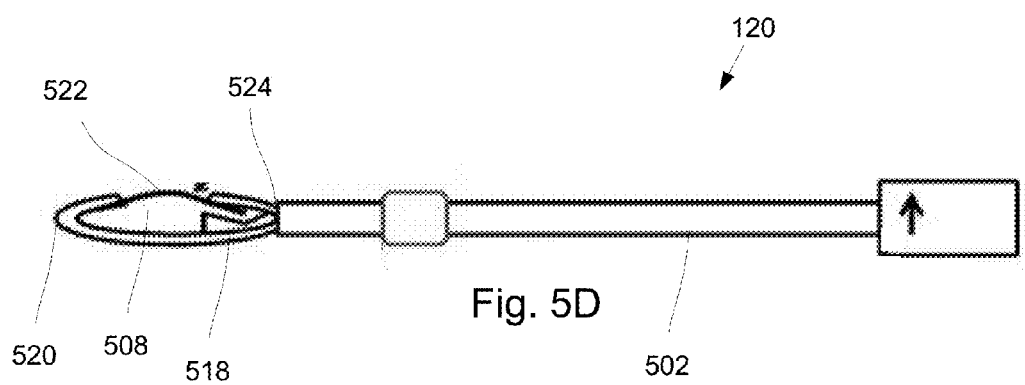

FIG. 5D shows another embodiment of a trapping device 120. In FIG. 5D, opening 508 is located within a clasping end 518. Clasping end 518 may be a separate mechanism coupled to body 502, or it may be integral to body 502. The distal end 520 may be shaped or sharpened to allow tunneling through subcutaneous tissue. Clasping end 518 can also include a strip 522 to facilitate trapping of capture device 104, as described above.

In some embodiments, clasping end 518 may be extendable from within body 502. In such an embodiment, when clasping end 518 is retracted, the distal end 524 may be used to dissect tissue as trapping device 120 is advanced to the site of fascial opening 102.

Figure 6A:
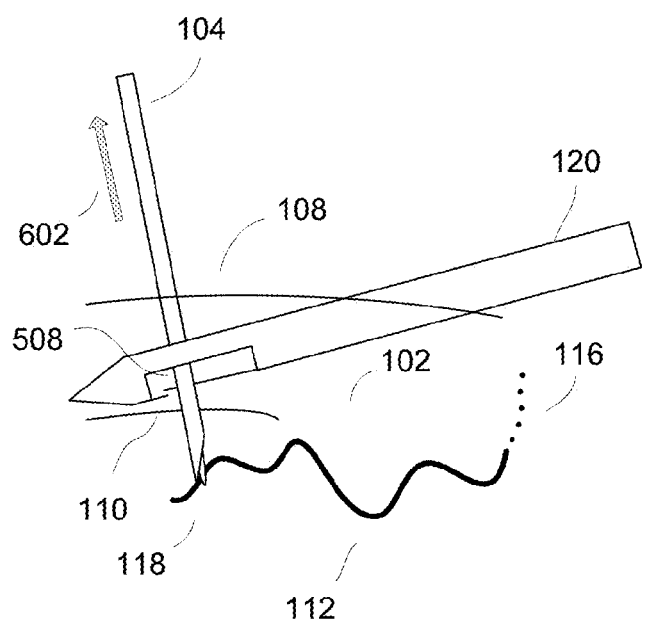
FIGS. 6A-6C show a trapping device engaging a suture at the site of the fascial opening.
Figure 6B:
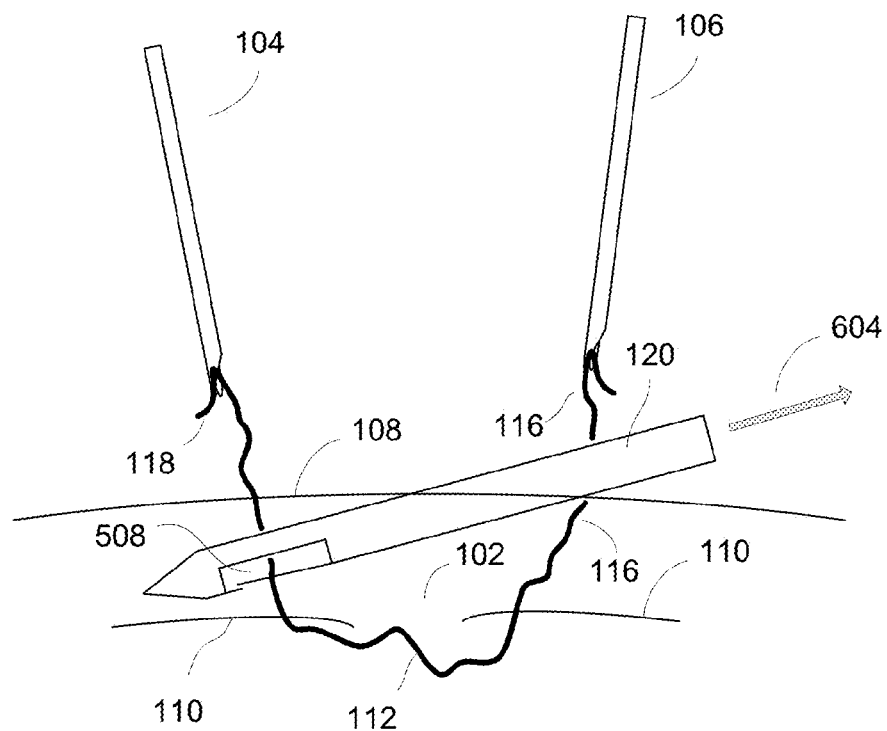
Figure 6C:
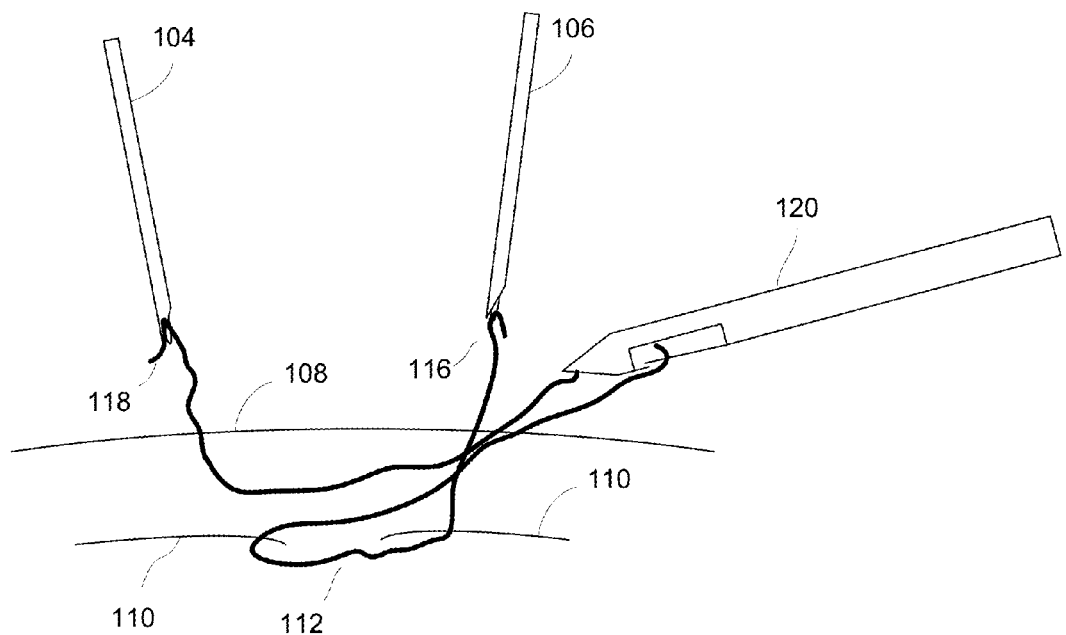

FIGS. 6A-6C illustrate how trapping device 120 may be used to locate and trap capture device 104. As shown in FIG. 6A, trapping device 120 may tunnel and dissect its way through tissue to a position between skin 108 and fascial tissue 110. Trapping device 120 and/or capture device 104 can provide tactile feedback to a user so that the user knows when trapping device 120 and capture device 104 come in contact with each other under the skin. For example, as a user advances trapping device 120 under the skin, trapping device 120 can be used as a probe to locate capture device 104. When contact is made, the user holding trapping device 120 and/or capture device 104 may feel the contact so he or she can subsequently use trapping device 120 to trap capture device 104.

Once trapped, capture device 104 may be withdrawn in the direction shown by arrow 602 so that suture 112 becomes threaded through opening 508, as shown in FIG. 6B. Trapping device may then be retracted in the direction shown by arrow 604 in order to pull the trapped portion of suture 112 toward proximal end 116 of suture 112, as shown in FIG. 6C. This may allow suture 112 to be subsequently tied, and fascial opening 102 closed.

Figure 7:
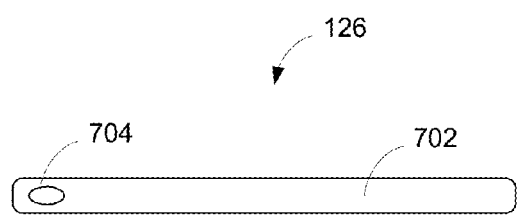
FIG. 7 depicts a knot pusher device for use in tying a suture.

Looking now at FIG. 7, to facilitate such tying and securing of suture 112, system 100 may also include a knot pusher 126. Knot pusher 126 may include a body 702 having a hole 704 in its distal end. Body 702 may be sufficiently rigid so that, as a surgeon ties knots in suture 112, body 702 can push the knot along suture 112 and underneath the skin to the site of fascial opening 102, where it can be secured. Of course, other knot pusher designs may be used as well.

Since the various devices described above in connection with fascial closure system 100 may be designed to be inserted into the body of a human or animal, the devices can be made, in whole or in part, from a material that is biocompatible. The biocompatibility of the material may help minimize occurrence of adverse reactions due to use within the body of the patient. The various devices may further include one or more coatings on an outer and/or inner surface to reduce infection in the patient, and/or control friction as the devices are used during surgery.

Additionally, since suture 112 may remain within the body after surgery, suture 112 can be made from a material that is bioabsorbable, so that suture 112 is absorbed and/or disintegrated over time.

Example of Operation

The systems, apparatuses, and methods described can be used to repair, for example, a ventral or abdominal wall hernia. In some instances, they may be used to laparoscopically repair a hernia using the components separation method ("CSM"). For example, a laparoscopic CSM may be used to align or shift the fascial opening toward the abdominal midline. Once the defect is aligned, the fascial closure systems described above may be used to close the defect.

Figure 8A:
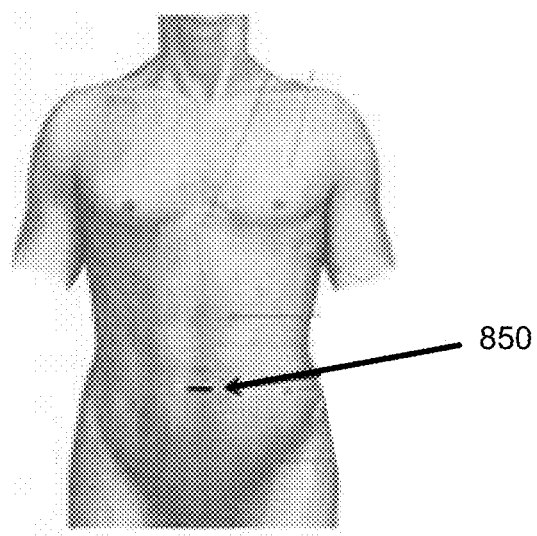
FIGS. 8A-8C illustrate a laparoscopic technique of repairing a fascial opening.

Aligning the Fascia using a laparoscopic CSM technique:

First, as shown in FIG. 8A, a surgeon may perform a small (e.g. about 2 cm), infra-umbilical skin incision 850, then bluntly dissect the incision to expose the anterior rectus sheath. A trocar may then be inserted to insufflate gas, and the blunt dissection may be extended over the anterior of the abdomen using, for example, a laparoscope and a hook dissector that can perform electrocautery coagulation of the blood vessels.

Figure 8B:
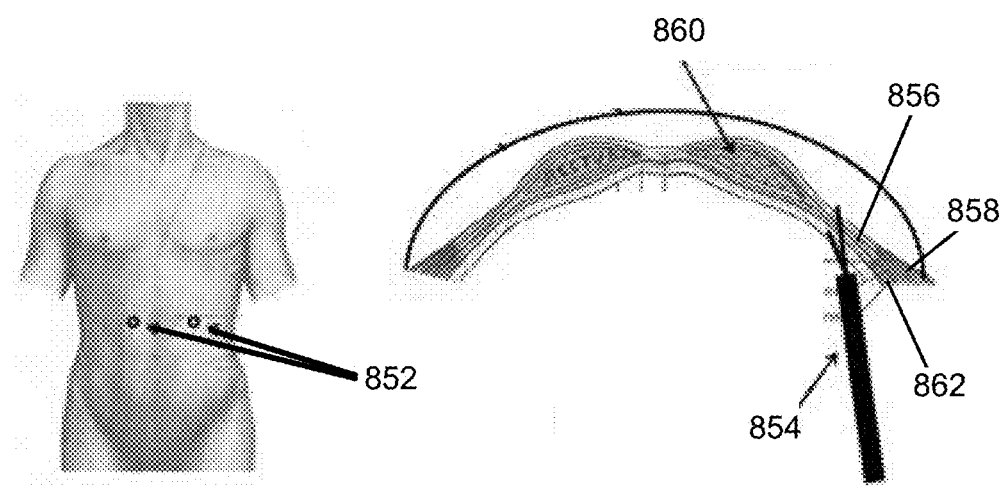

Turning to FIG. 8B, trocars may be inserted bilaterally through the skin, on opposing sides of the fascial defect, and into the subcutaneous cavity in the mid-clavicular line in the subcostal region, as shown by trocar sites 852. Laparoscopic shears 854 may then be inserted through the trocars in order to incise the aponeurosis 856 of the external oblique muscle 858. In some embodiments, the incision or incisions may be about 1-2 cm lateral to the border of the rectus abdominus muscle 860.

Once the incision or incisions are made, the surgeon may remove one of the trocars and bluntly dissect through the external oblique muscle 858 in order to expose the internal oblique muscle 862. Once exposed, the surgeon may reinsert the trocar, insufflate the cavity, and bluntly dissect the external oblique muscles 858 from the internal oblique muscles 862 using, for example, a rigid, laparoscopic rod. Once the external oblique muscles 858 and internal oblique muscles 862 are separated, the surgeon may repeat the process and dissect the muscles on the other side of the abdominal midline.

Figure 8C:
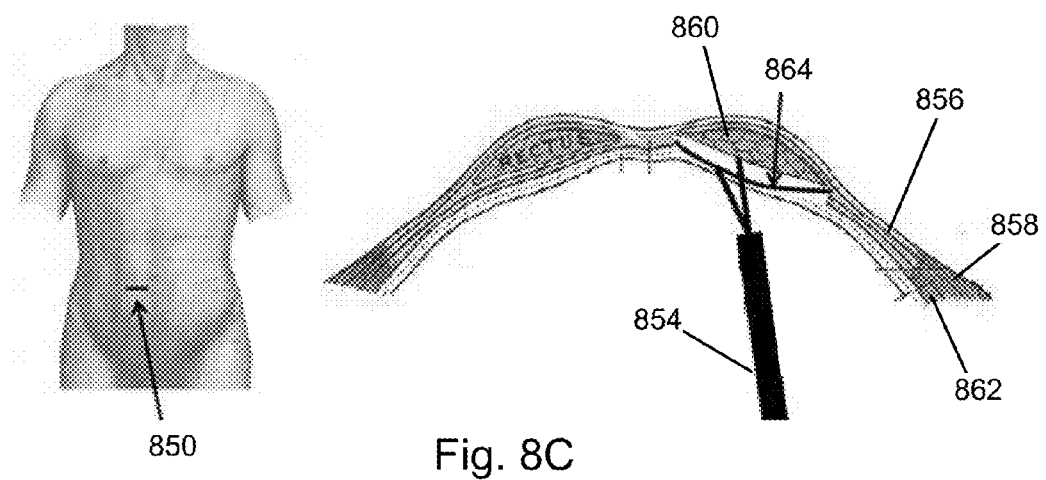

If needed, the surgeon may make an incision on the posterior rectus sheath. For example, as shown in FIG. 8C, the surgeon may displace the infra-umbilical trocar port incision 850 laterally and make a small (e.g. about 2 cm) incision on the anterior rectus sheath. The rectus muscle 860 may then be bluntly dissected through the incision to expose the posterior rectus sheath 864. An object (e.g. a finger or laparoscopic device) may be inserted to create a cavity between the rectus muscle 860 and the posterior rectus sheath 864. The trocar port 850 may then be moved back to the abdominal midline and a trocar may be inserted to insufflate the cavity. Using an endoscopic blunt rod or similar device, the surgeon may then dissect the rectus muscle 860 from the posterior rectus sheath 864, inferiorly and superiorly, for example. Laparoscopic shears 854 may then be inserted through the incision 850 and incise the posterior rectus sheath 864 longitudinally.

Once the muscles and rectus sheaths have been separated from each other, the muscles and fascia can be shifted to the abdominal midline, so the defect can be laparoscopically closed with a suture as described below, without incurring a high degree of tension or pulling against the suture.

Closing a Fascial Opening Laparoscopically

FIGS. 9A-9F show an example of a fascial closure system 100 laparoscopically delivering a suture to the site of a fascial opening, and subsequently tensioning the suture in order to close the opening. These figures show skin 108 and fascial tissue 110, but do not show muscle, fat, and other tissue layers for simplicity of description. However, one skilled in the art will recognize that various tissue layers may exist between the skin 108 and fascial tissue 110, including muscle, fat, fascia, aponeurosis, etc.

Figure 9A:
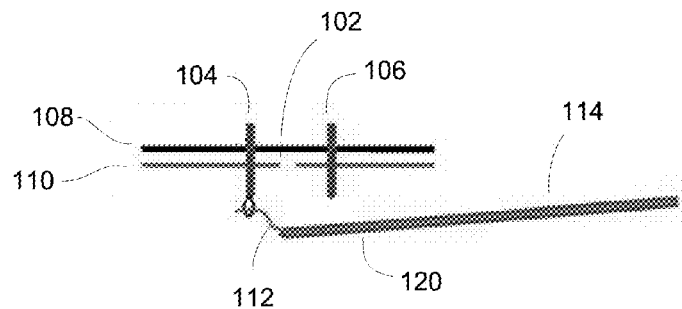
FIGS. 9A-9F illustrate an example of the system of FIG. 1 used to close a fascial opening.

As shown in FIG. 9A, suture capture devices 104 and 106 may be inserted through skin 108 and fascial tissue 110 on opposing sides of a fascial opening 102. Delivery device 114 may then be advanced to the site of the fascial opening 102 to position suture 112 posterior to the fascial tissue 110, and near capture device 104 for delivery. Suture capture device 104 may then grasp and hold the end of suture 112. Although not shown, delivery device 114 may then deliver a proximal end of suture 112 to suture capture device 106 so that suture capture device 106 can grasp and hold the proximal end of suture 112. Delivery device 114 may then be retracted from the site of fascial opening 102, allowing suture 112 to exit from within the body delivery device 114, so that suture 112 can remain in place, held by suture capture devices 104 and 106 at the site.

Figure 9B:
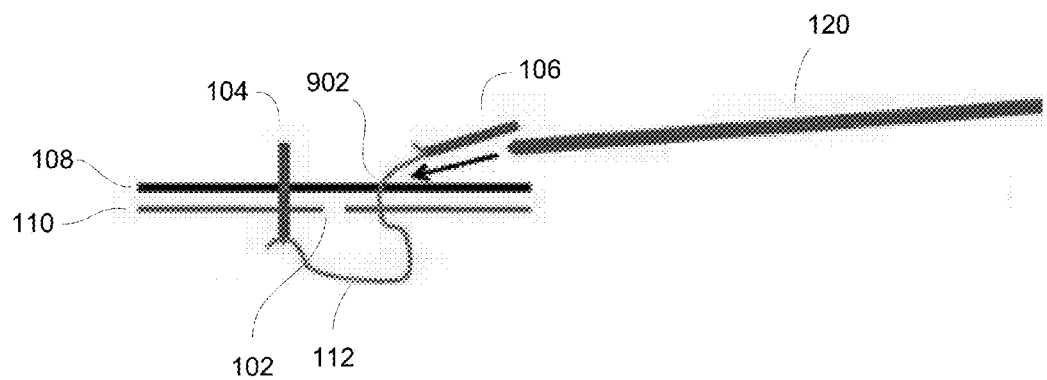
Figure 9C:
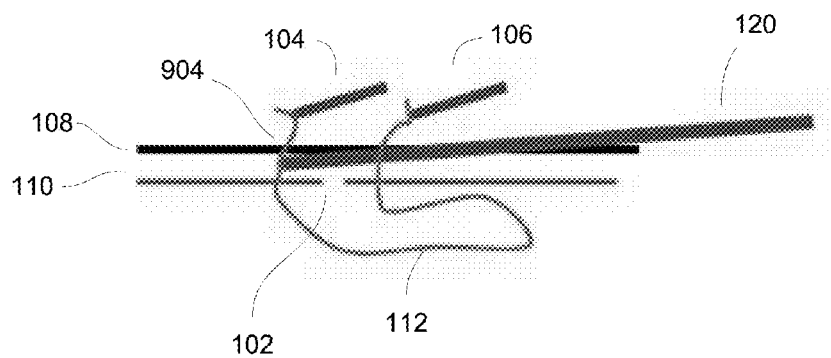

After suture 112 is delivered, suture capture device 106 can be refracted from the site, as shown in FIG. 9B, and thread suture 112 through fascial tissue 110 at the proximal side of fascial opening 102. As shown, suture capture device 106 may draw the proximal end of suture 112 outside the body through incision 902. Trapping device 120 may then be directed into the body through, for example, the incision 902 recently vacated by suture capture device 106, and advanced across fascial opening 102 to a position between skin 108 and fascial tissue 110 on the distal side of fascial opening 102. As it is advanced, trapping device 120 can dissect and/or tunnel through intervening tissue between incision 902 and capture device 104. Once advanced, trapping device 120 can then trap capture device 104 within gap 508, as described above. Capture device 104 can then be retracted from the site so that suture 112 becomes threaded through fascial tissue 110, through the opening in trapping device 120, and through incision 904, as shown in FIG. 9C.

Figure 9D:
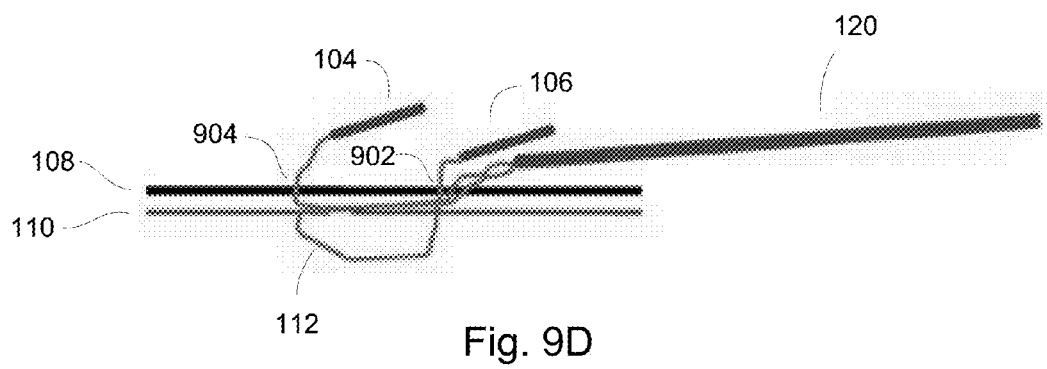

After capture devices 120 are retracted, the distal end of suture 112 may extend from incision 904, while the proximal end may extend from incision 902. However, in order to facilitate tying suture 112 so the knot is placed beneath the skin, both ends of suture 112 should extend from the same incision 902. Therefore, trapping device 120 may be withdrawn through incision 902 so that it pulls the distal portion of suture 112 through incision 902 and toward the proximal end of suture 112, as shown in FIG. 9D.

Figure 9E:
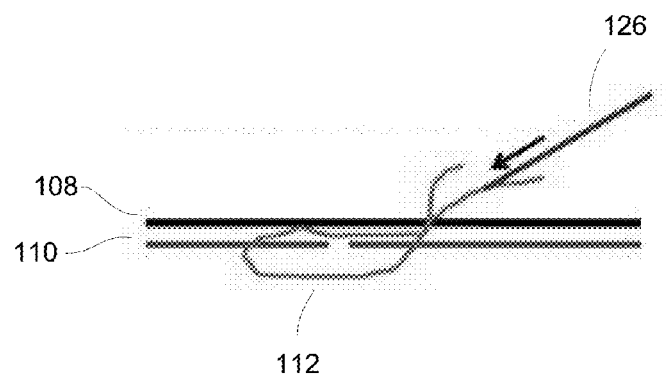
Figure 9F:
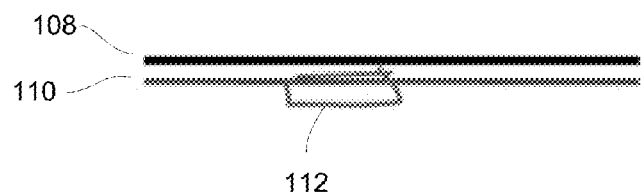

Once both the distal and proximal ends are extending through incision 902, suture capture devices 104 and 106 can release suture 112, and any excess length of suture 112 may be cut and removed. The ends of suture 112 may then be tied, as shown in FIG. 9E. Knot pusher 126 may then be used to maintain tension on suture 112 and push knot 1006 toward fascial opening 102, so that fascial opening 102 can be closed and suture 112 secured in place, as shown in FIG. 9F.

Multiple sutures may be delivered to the fascial opening, and the process may be repeated as many times as necessary in order to close the fascial opening. A large fascial opening, for example, may require delivery of multiple sutures which can be tied parallel to each other along the length of the opening. The system 100 may be re-used in order to deliver multiple sutures to the site, or may be discarded, in whole or in part, after delivery of a single suture, so that a fresh system 100 can be used to deliver a subsequent suture. Whether to use the system 100 to deliver a single suture or multiple sutures depends upon the application.

Although the present invention(s) have been described in terms of one or more embodiments, one skilled in the art will recognize that the embodiments are examples of the invention and are not intended to limit the scope. Rather, variations and alternative embodiments may fall within the scope of the claimed invention(s).

What is claimed is:

1. A system for closure of a fascial opening, the system comprising:
   a first capture device having a hook at its distal end for retaining and pulling one end of a suture through fascial tissue on one side of a fascial opening;
   a second capture device having a hook at its distal end for retaining and pulling an opposing end of the suture through the fascial tissue on an opposite side of the fascial opening;
   a trapping device having an opening near its distal end that the first or second capture device can enter for locating and engaging the first or second capture device prior to the capture device being pulled through the fascial tissue so that the first or second capture device can subsequently thread the suture through the opening such that the suture can be subsequently pulled by the trapping device.

2. A system as set forth in claim 1, wherein the trapping device includes a trap that allows the first or second capture device to enter the opening, and minimizes the occurrence of the first or second capture device exiting the opening, so that the trapping device can retain the first or second capture device within the opening.

3. A system as set forth in claim 2, wherein the trap is one of: a clasp, a slot, or a combination thereof.

4. A system for closure of a fascial opening, the system comprising:
   a first capture device having a hook at its distal end for retaining and pulling one end of a suture through fascial tissue on one side of a fascial opening;
   a second capture device having a hook at its distal end for retaining and pulling an opposing end of the suture through the fascial tissue on an opposite side of the fascial opening;
   a trapping device having an opening near its distal end for locating and engaging the first or second capture device prior to the capture device being pulled through the fascial tissue so that the suture can be subsequently pulled by the trapping device; and
   a delivery device for placing the ends of the suture on the opposite sides of the fascial opening so they can be captured by the first and/or second capture devices.

5. A system as set forth in claim 4, wherein the delivery device includes an extension for presenting the ends of the suture for capture at the site of the fascial opening.

6. A system as set forth in claim 4, wherein the delivery device includes a fastener that holds the ends of the suture during advancement of the delivery device, and positions the ends of the suture at the site of delivery for capture.

* * * * *